United States Patent
Robinson (10) Patent No.: US 8,478,016 B2
(45) Date of Patent: Jul. 2, 2013

(54) RADIOGRAPHIC DATA INTERPRETATION

(75) Inventor: Max Robinson, Shincliffe (GB)

(73) Assignee: Kromek Limited, Durham (GB)

( * ) Notice: Subject to any disclaimer, the term of this patent is extended or adjusted under 35 U.S.C. 154(b) by 114 days.

(21) Appl. No.: 13/120,630

(22) PCT Filed: Sep. 16, 2009

(86) PCT No.: PCT/GB2009/051201
§ 371 (c)(1),
(2), (4) Date: Apr. 19, 2011

(87) PCT Pub. No.: WO2010/035023
PCT Pub. Date: Apr. 1, 2010

(65) Prior Publication Data
US 2011/0188727 A1    Aug. 4, 2011

(30) Foreign Application Priority Data
Sep. 24, 2008 (GB) .................................. 0817487.2

(51) Int. Cl.
*G06K 9/00* (2006.01)
(52) U.S. Cl.
USPC ........................................................ 382/132
(58) Field of Classification Search
None
See application file for complete search history.

(56) References Cited

U.S. PATENT DOCUMENTS

| | | | |
|---|---|---|---|
| 5,943,388 A | 8/1999 | Tumer | |
| 6,018,562 A * | 1/2000 | Willson | 378/9 |
| 7,362,847 B2 * | 4/2008 | Bijjani | 378/57 |
| 7,545,902 B2 * | 6/2009 | Hoffman | 378/5 |
| 7,634,051 B2 * | 12/2009 | Robinson | 378/41 |
| 8,014,493 B2 * | 9/2011 | Roux et al. | 378/56 |
| 8,098,794 B1 * | 1/2012 | Fernandez | 378/57 |
| 8,116,428 B2 * | 2/2012 | Gudmundson et al. | 378/53 |
| 8,233,588 B2 * | 7/2012 | Gibson et al. | 378/53 |
| 2006/0078085 A1 * | 4/2006 | Zanker | 378/57 |
| 2008/0069295 A1 | 3/2008 | Hoffman | |

FOREIGN PATENT DOCUMENTS

| | | |
|---|---|---|
| EP | 0 261 984 | 3/1988 |
| GB | 2 390 005 | 12/2003 |
| WO | WO 2008/119967 | 10/2008 |

OTHER PUBLICATIONS

XP006507515, Evans JPO et al.; "3-D X-ray image modeling latest developments," Security and Detection, Ecos 97, European Conference on London dated Apr. 28, 1997, pp. 1-4.
XP010819703, Cajipe V B et al.; "Multi-energy X-ray imaging with linear CZT pixel arrays and integrated electronics," Nuclear Science Symposium Conference Record, 2004, IEEE, Piscataway, NJ, USA, vol. 7, dated Oct. 16, 2004, pp. 4548-4551.

(Continued)

*Primary Examiner* — Nancy Bitar
(74) *Attorney, Agent, or Firm* — Drinker Biddle & Reath LLP (57) ABSTRACT

A method and apparatus are described for the collection and interpretation of radiographic data from an object scanned by a suitable radiation source. A radiation detector system is provided that is detecting and collecting spectroscopically resolved information. An object is scanned from a plurality of perspectives, and the resultant data from each perspective resolved into at least three spectroscopic energy bands. For each such resolved spectroscopic energy band an image analysis is performed to derive depth slicing to produce a series of output datasets each comprising a 2-D dataset of intensity information resolved to a single energy band and depth slice.

18 Claims, 4 Drawing Sheets

OTHER PUBLICATIONS

XP006020222, Wang T W et al., "Stereoscopic dual-energy X-ray imaging for target materials identification," IEE proceedings: Vision, Image and Signal Processing, Institution of Electrical Engineers, GB. vol. 150. No. 2, dated Apr. 24, 2003, pp. 122-130.

XP025053164, Evans J P O et al., "View Synthesis for depth from motion 3D X-ray imaging," Pattern Recognition Letters, Elsevier, Amsterdam, NL, vol. 27, No. 15, dated Nov. 1, 2006, pp. 1863-1873.
International Search Report and Written Opinion, dated Jan. 2010.
UK Search Report dated Feb. 23, 2009.

* cited by examiner

RADIOGRAPHIC DATA INTERPRETATION

FIELD OF INVENTION

The invention relates to a method and apparatus for the collection and interpretation of radiographic data, and especially x-ray interaction data, using resolved spatial and energy information. The invention thereby relates to a method and apparatus for the inspection and characterisation of objects in three-dimensional space, for example where it is desirable to gain information about internal contents and/or composition. The invention may further relate to a method and apparatus that operates by or in conjunction with the generation of an image of the material, but is not limited to such imaging.

BACKGROUND

The principle of scanning objects with high energy radiation such as x-rays or gamma-rays is widely employed in circumstances where it might be desirable to gain information about the internal contents and/or composition of an object, including for example scanning for identification purposes, for stock control purposes, to monitor changes and especially degradation over time, in a security or like situation for the detection of dangerous or prohibited materials, for example to screen persons or baggage for entry into or exit from a restricted area, for quality control purposes or the purposes of determining the integrity of the structure, or the like.

Most objects that are x-rayed consist of a variety of materials, compounds tissues etc. They are also usually three dimensional in nature but despite this ordinary radiographs are simply flat shadowgraph images which contain only monochrome intensity information. X-ray sources are almost always broad spectrum emitters of radiation. However most detector types are unable to resolve this energy information. Radiographs produced in this way have therefore all the spatial information and all the energy information collapsed into a single 2-D plane. This means that if one is interested in only seeing information inside an object at a particular depth and consisting of a certain type of material, this will always be set against a backdrop of clutter in the image caused by objects in the same x,y region and consisting of other types of materials.

Recent development of detectors that can resolve spectroscopic information about the transmitted x-rays more effectively has led to the development of apparatus that discriminate across a plurality of energy bands to generate a plurality of energy-differentiated images. For example U.S. Pat. No. 5,943,388 describes a system that makes use of cadmium telluride detectors to image across at least three energy bands and generate at least three images. Radiographs produced in this way have some differentiation energy information but all the spatial information remains collapsed into a single 2-D plane.

A method and apparatus have been proposed in application No PCT/GB2008/001103 for the production of monocular movement parallax x-ray images. The architecture of the system must be such that the series of images so produced contain only disparity information in the horizontal direction (i.e. the direction of the separation of the human eyes). Presenting this sequence of images to a human observer will give the same effect as rotating the object. This series of perspective images have contained within them three dimensional coordinate data. In much the same way that photogrammetry can be applied to stereoscopic pairs of images by measuring disparity between perspectives views, so too can it be applied to the series of monocular movement parallax images. A big advantage of doing this is that the more images there are and the greater the disparities involved, then the more accurately the depth or z coordinate can be calculated. A limitation of using stereo pairs is that there is a very tightly controlled limit on the disparity that can be used which effectively limits the depth resolution that can be obtained.

Nevertheless, it remains desirable to develop a method and apparatus for the collection and interpretation of radiographic data that makes effective use of both the spatial information and the energy information collected radiographically by selective energy detectors in a resolved co-ordinated manner.

SUMMARY OF THE INVENTION

In accordance with the invention in a first aspect there is provided a method for the collection and interpretation of radiographic data from an object comprising the steps of:

providing a radiation source and a radiation detector system spaced therefrom to define a scanning zone therebetween in such manner as to define at least first and second laterally spaced scanning positions, the detector system being capable of detecting and collecting spectroscopically resolvable information about radiation incident thereon;

causing an object to move relative to and through the scanning zone across the laterally spaced scanning positions; and thereby generating at least a first perspective dataset of intensity information from the detector output at the first scanning position;

generating at least a second perspective dataset of intensity information from the detector output at the second scanning position;

resolving each perspective dataset into at least three spectroscopic energy bands;

for each such resolved spectroscopic energy band:

performing a numerical image analysis of data from each perspective dataset to identify corresponding points in different perspective dataset;

thereby obtaining numerical data concerning disparity between each perspective dataset;

thereby obtaining z-coordinate information using triangulation and using the z-coordinate information to divide each perspective dataset at each energy band into a plurality of depth slices;

and thereby producing a series of output datasets each comprising a 2-D dataset of intensity information resolved to a single energy band and depth slice.

By analogy, in accordance with a further aspect of the invention, there is provided an apparatus for the collection and processing of radiographic data from an object comprising:

a radiation source and a radiation detector system spaced therefrom to define a scanning zone therebetween configured in such manner as to define at least first and second laterally spaced scanning positions, the detector system being capable of detecting and collecting spectroscopically resolvable information about radiation incident thereon;

a data collection module to collect in use at least a first perspective dataset of intensity information from the detector output at the first scanning position and at least a second perspective dataset of intensity information from the detector output at the second scanning position;

an energy resolution module to process and resolve each perspective dataset into at least three spectroscopic energy bands within the spectrum of the source;

a spatial resolution means including an image analyser module to numerically analyse, for each such resolved spectroscopic energy band, data from each perspective dataset to identify corresponding points therein, a disparity module to obtain therefrom numerical data concerning disparity between each perspective dataset; and a depth slicing module to resolve z-coordinate information therefrom using triangulation to divide each perspective dataset at each energy band into a plurality of depth slices;

an output data register to store output data generated by the spatial resolution module as a series of output datasets each comprising a 2-D dataset of intensity information resolved to a single energy band and depth slice.

The radiation source comprises a source to deliver high-energy radiation such as ionizing radiation, for example high energy electromagnetic radiation such as x-rays and/or gamma rays, or subatomic particle radiation, and the detection system is adapted correspondingly to detect radiation in this spectrum. In accordance with the invention, intensity data from an interaction between radiation such as x-rays, gamma rays or the like and an object in the scanning zone, involving for example transmission, scattering, backscattering, absorption etc, is thus collected in a generally conventional manner. For most applications, it will be preferred that intensity data is obtained at least of transmitted radiation intensity, as would be the case for example to generate a transmission radiograph.

For each "scanning event" (that is, for a measurement of intensity via a given radiation path incident upon and for example passing through a given object in a given scanning position) an "intensity dataset" is collected representing the collected intensity incident at the detector across at least part of a source energy spectrum. Typically, intensity data is collected across an area (i.e. with x,y co-ordinates), although this could in principle be effected by an area scan, line scan or even single pixel detector system with appropriate scanning methodology.

If such a dataset were presented simply as an image, as in basic radiography, any spatial information and energy information inherent in the collected data is collapsed into a single 2-D plane. This means that information inside an object at a particular depth and/or consisting of a certain type of material will always be set against a backdrop of clutter in the image caused by objects in the same x,y region and consisting of other types of materials.

However, in accordance with the invention, both spectrally selective information and z-co-ordinate information are extracted to produce an output dataset with improved differentiation of both the spatial information and the energy information.

First, a detection system is used which is capable of detecting intensity data for a given "scanning event" in at least three separate energy bands across the spectrum of the source. The detector system is capable of detecting and resolving intensity data for a given "scanning event" in the sense that it is adapted to differentiate incident radiation simultaneously into at least three separate energy bands across the spectrum of the source. For example, the detector system exhibits a spectroscopically variable response across at least a part of the source spectrum allowing such simultaneous differentiation of incident radiation into at least three energy bands. A perspective dataset thus constitutes a dataset of intensity information related to frequency/energy which is resolvable into at least three such bands to produce at least three intensity datasets relating to a given scanning position for an object/material under test.

The method in a first step comprises resolving this perspective dataset into at least three spectroscopic energy bands such that, for each of the at least two perspective views (i.e. at each scanning position) intensity data is processed into at least three energy bins. A more preferred number might be 8 or 16.

The apparatus comprises an energy resolution module to effect this step, for example comprising a data processing module to distinguish spectroscopically resolved intensity data and a data storage module to store this intensity data in a suitable plurality of energy bins.

Second, use is made of the fact that data is collected of intensity information across two dimensions (x,y co-ordinate) from the detector output from at least two perspectives, representing the first and second scanning positions. Thus, for each resolved energy band there is at least one pair of datasets of intensity information across two dimensions. A numerical analysis of the positional disparity between features of these, and especially a numerical analysis of monocular parallax between pairs of datasets, may be used to resolve z-coordinate information using triangulation in a manner which will be generally familiar.

Measurement of disparity in the collected data from different perspectives involves identifying corresponding points in each perspective view. This can in fact be quite difficult in complex images. However using the imaging geometry essential for stereoscopic imaging or monocular movement parallax imaging puts a very important constraint on where to search for the corresponding points. This is known as the epipolar line constraint. The concept is established. In simple terms, the epipolar line runs through each of the sequence of images at the same horizontal level.

Preferably, the step of numerically identifying disparity in the collected data from different perspectives makes use of the epipolar line constraint. It is known in image analysis to use appropriate algorithms that search for corresponding features such as edges along this epipolar line. Once these are found then z coordinate information can be calculated using triangulation. Any dataset can be divided in this way into a suitable plurality of notional "depth slices", in which data is resolved to give intensity information separately for each notional depth slice.

The invention is particularly characterised in that this depth resolution step is carried out for each energy band using data from plural perspective views separated at equivalent energy bands. Thus, the resultant output dataset includes separate maps of 2-D intensity information for each energy band at each notional depth slice. This may be combined to produce an output dataset having 3-D intensity information for each energy band.

For example if images are to be displayed, since the volumetric data is now resolved on the series of depth planes it will be possible to remove layers in the image to view depth regions of interest. Additionally or alternatively energy bands which contain information which is not of interest can also be removed. Thus a region in an object of particular interest can be viewed without having any clutter associated with it caused by either overlying or underlying information. Images may be viewed of depth planes at any energy or combination of energies and/or of energy planes at any depth or combination of depths. It still remains possible also to view images from data maps at different perspectives simultaneously or sequentially for example to present monocular parallax information visually to a viewer. More of the information inherent in the original unresolved dataset is made available in a more accessible way.

As well as viewing depth regions of interest separately it would also be possible to build up a volume rendered model using the depth plane slices in much the same way that known for computed tomography (CT).

Therefore, in a preferred embodiment the method further comprises the generation of an image dataset from at least some and preferably all of the output datasets having x,y spatial, energy and depth slice resolution. Thus, multiple images may be generated of an object moving through the scanning zone. The method of the invention conveniently further provides the additional step of displaying images from such image datasets and for example displaying such images as separate simultaneously or sequentially and/or as composite images on a suitable display means such as a visual display screen.

By analogy, in a preferred embodiment the apparatus includes an image generation module to generate an image dataset from at least some and preferably all of the output datasets having x,y spatial, energy and depth slice resolution, and optionally further a data register for the storage of such image datasets and or image display means on which may be displayed images from such image datasets.

The display means is conveniently a simple two dimensional display screen, for example a conventional video display screen (which term is intended to encompass any direct display or projection system exploiting any cathode ray tube, plasma display, liquid crystal display, liquid crystal on silicon display, light emitting diode display or like technology). It is a particular advantage that the method can be envisaged for use with, and the apparatus for the invention incorporated into, the standard display screens of comparable existing systems for example in the security or medical imaging fields.

For clarification it should be understood that where used herein a reference to the generation of image dataset is a reference to the creation of information dataset, for example in the form of a suitable stored and manipulatable data file, from which a visual representation of the resolved energy/intensity/spatial data for the object under investigation could be produced, for example representing intensity and/or energy by variations of image intensity/colour/hue etc in the image and representing spatial resolution as spatial resolution in the image. References to displaying this image are references to presenting an image generated from such a dataset in a visually accessible form, for example on a suitable display means.

In accordance with the invention, the use of plural laterally spaced scanning positions creates a monocular parallax between otherwise equivalent image pairs or series.

In one possible embodiment the method comprises displaying such image pairs or series successively and thus displaying the monocular movement parallax between the images. Similarly in one possible embodiment the apparatus comprises an image display adapted successively to display such images and thus display the monocular movement parallax between the images.

The method and apparatus of the invention thus produces an output dataset with enhanced flexibility in regard to any such imaging.

Moreover, the advantage is not merely in the ability to resolve the information in these two ways in the output dataset. There is a synergy in the data processing stage which confers further advantage over either resolution technique considered in isolation.

Although using the epipolar line constraint is a very useful tool it can still be very difficult to identify corresponding points on the line in complex images.

However in accordance with the present invention the series of perspective views is first resolved into a series of energy selective perspectives. The matching of corresponding points on the epipolar line is then greatly simplified. If the whole image is analysed in this way a composite 3-D model can be produced having a series of depth planes or slices that resolves more fully the potential spatial and energy information contained in each initial scan.

If there are more than two perspective views the data available for application of this method is increased. Preferably therefore, the method of the invention involves generating at least one further perspective dataset of x,y co-ordinate intensity information, and the apparatus is suitably adapted to do so.

For example if there were 3 perspective views which could be resolved into 8 energy bands each, then there would be a total of 24 distinctly different images. By working with each set of 3 perspective views at a particular energy it is possible to produce a volumetric separation of the object that has been x-rayed. There would in fact be 8 volumetric models corresponding to the 8 energy bands that were used. All 8 volumetric models could then be combined on a depth plane by depth plane basis so producing a complete model which has been recombined from the energy information and spatial details segmented from it.

There are two ways in which additional perspective datasets can be generated. First, the radiation detector system may be configured in such manner as to define further laterally spaced scanning position(s). It may be configured to define further laterally spaced scanning positions either in the form of discrete detector units or in the form of separately addressable areas of a composite detector unit. The output of the detector at each spaced scanning position may then be used singly to generate a perspective dataset representative of data collected at the detector for each spaced scanning position.

In one possible embodiment there may be provided a laterally spaced series of linear detectors, for example at least three detectors, and more preferably at least five detectors.

Where a plural series of laterally spaced linear detectors is provided, the space in between them is preferably generally constant, for example in that each pair of adjacent linear detectors in the series is substantially equally laterally spaced and/or at a substantially equal angular spacing relative to the source.

The linear detectors making up the laterally spaced series are preferably generally parallel. They may be disposed in a common plane or along a common arc. Each linear detector may be of any suitable configuration, for example of a conventional simple or folded configuration.

Preferably the linear detectors making up the laterally spaced series are arranged such that the distance between them changes in order to maintain a constant angular separation between each array. This is of critical importance for L-shaped detectors which are commonly found in many scanning industries. This innovation is also of critical importance when the source is not positioned at the central point of each array.

Preferably the apparatus comprises alignment means to allow for precise alignment of each linear detector as above described.

Preferably the apparatus comprises means to deliver plural beams, preferably from a single source. For example a beam is directed at each scanning position. Preferably the means to deliver plural beams allows a user to select a desired number of beams to correspond to the number of scanning positions.

Additionally or alternatively, further perspective datasets may be generated by interpolation of pairs of datasets collected from adjacent scanning positions. Thus, in accordance with a possible embodiment of the invention, the method additionally comprises generating at least one intermediate dataset from measured datasets from at least one adjacent pair of scanning positions, and where applicable preferably generating at least one intermediate image from a plurality of adjacent pairs and for example each adjacent pair, of scanning positions, by processing the output of the detector(s) at the or each said pair of positions and generating a virtual perspective dataset representative of an output intermediate between the two said detected outputs.

The apparatus of the invention preferably includes a virtual perspective dataset generator comprising a means having this functionality.

Where a single intermediate perspective dataset is generated between an adjacent pair of detected datasets, the intermediate perspective dataset preferably extrapolates to a midpoint between equivalent points on the two detected datasets. Where a plurality of intermediate datasets is provided between a pair of detected datasets these are preferably based on a similar, evenly spaced extrapolation.

In accordance with the foregoing, either or both approaches is used to generate a series of datasets of an object in a scanning zone in what amounts, in effect, to different positions. In the first approach, a lateral array of spaced scanning positions is defined, and for example a plurality of spaced detectors is provided, to produce a corresponding plurality of detected direct datasets. In the second approach, data from adjacent scanning positions is used to generate an indirect dataset intermediate to the direct datasets.

The detector system is adapted to generate spectroscopic information about the transmitted radiation at least to the extent of resolving at least three and preferably at least five energy bands. It may be convenient to resolve the output into 8 or 16 such energy bands.

So long as plural specific energy bands are resolved, the bandwidth is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy "band" includes evaluation of intensity at such a discrete single energy as well as evaluation of intensity at an energy across a narrow or broad bandwidth. However, the same energy bands are generally used for each perspective dataset.

A detector system in accordance with the invention may comprise a single detector or a plurality of discrete detector elements making up a multi-element system. An area detector may be made up of a 2-D array of discrete detector elements and/or of a 2-D array of separately addressable pixels on a compound element. A linear detector may comprise a linear array of discrete detector elements and/or an array of separately addressable pixels on a linear compound element. A detector may additionally be capable of resolving incident radiation spatially by any combination of inherent resolution as above and raster scanning.

It is necessary that the detector system is enabled to detect radiation in a manner which is spectroscopically resolvable by the data processing apparatus. Preferably, the detector system exhibits a spectroscopically variable response across at least a substantial part of the spectrum of the radiation source allowing detailed spectroscopic information to be retrieved. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum.

For example, the detector system or element comprises a semiconductor material or materials preferably formed as a bulk crystal, and for example as a bulk single crystal (where bulk crystal in this context indicates a thickness of at least 500 µm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_b Te$ where a and/or b may be zero.

Combination of these and any other such materials may be considered which give spectroscopic detection rather than merely detecting amplitude of radiation after interaction with a sample.

The source may be a single broad spectrum source across which a plurality of bandwidths or single energies may be identified. For example the source may be an x-ray source. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

The source is preferably capable of generating a sufficiently broad spectrum of radiation to enable the spectral resolution necessary for the performance of the invention. Preferably the source generates radiation across at least one or more parts of the range of 20 keV to 1 MeV, and more preferably across at least a part, and for example a major part, of the range of 20 keV to 160 keV. For example the source generates radiation ranging across at least one bandwidth of at least 20 keV within the given range. For example the spectrum is such that at least three 10 keV bands can be resolved within that range.

The invention in particular relates to a method and apparatus operating on the line-scan principle, in which three dimensional objects are caused to move through a scanning zone and imaging information collected.

Imaging apparatus which employs the line-scan principle is well known. Typically, such apparatus will consist of a suitable source, the beam of which may be collimated into a curtain, usually referred to as a "curtain beam", and is then detected by a linear detector for example comprising a linear photodiode array. Image information is obtained by having the object of interest move linearly for example at right angles with respect to the beam and storing successive scans of transmission information derived from the linear array from which a complete image frame can be compiled.

Accordingly, in this embodiment, the method comprises:
providing a source and a detector system spaced therefrom to define a scanning zone therebetween, the detector system comprising a plurality of spaced linear detectors capable of generating spectroscopically resolvable information about incident radiation;
causing an object to move relative to and through the scanning zone to generate a corresponding plurality of 2-D perspective datasets in which intensity data is resolved across x,y co-ordinates;
resolving the resultant transmitted data in the manner above described.

Accordingly, in this embodiment, the apparatus comprises:
a source and a detector system spaced therefrom to define a scanning zone therebetween, the detector system comprising a plurality of spaced linear detectors capable of generating spectroscopically resolvable information about incident radiation, and means to generate and store from each linear scan a 2-D perspective dataset in which intensity data is resolved across x,y co-ordinates, allowing resolution of the resultant transmitted data in the manner above described In accordance with this embodiment the radiation source is preferably collimated to produce a curtain beam.

The source may comprise a single primary source adapted to generate a beam such as a curtain beam aligned to be incident upon each linear detector in the spaced serial array at a suitable angular separation, for example by a suitable beam splitting apparatus. A single beam may be generated. Alternatively, multiple beams may be generated from a single source. Alternatively, multiple sources may be provided each generating a beam such as a curtain beam incident upon a linear detector in the serial array. The source may comprise a source combining any or all of the foregoing principles.

Preferably the detector system comprises a plurality of linear detectors linearly or angularly spaced apart in generally parallel conformance in serial array. Each linear detector may comprise a linear array of detector elements.

It will be understood generally that a numerical step in the method of the invention can be implemented by a suitable set of machine readable instructions or code. These machine readable instructions may be loaded onto a general purpose computer, special purpose computer, or other programmable data processing apparatus to produce a means for implementing the numerical step specified. Similarly, a numerical analysis module may comprise a suitably programmed data processing apparatus such as a suitably programmed general purpose or special purpose computer or other programmable data processing apparatus.

Such machine readable instructions may also be stored in a computer readable medium that can direct a computer or other programmable data processing apparatus to function in a particular manner, such that the instructions stored in a computer readable medium produce an article of manufacture including instruction means to implement some or all of the numerical steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the numerical steps in the method of the invention. It will be understood that a step can be implemented by, and a means of the apparatus for performing such a step composed in, any suitable combinations of special purpose hardware and/or computer instructions.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
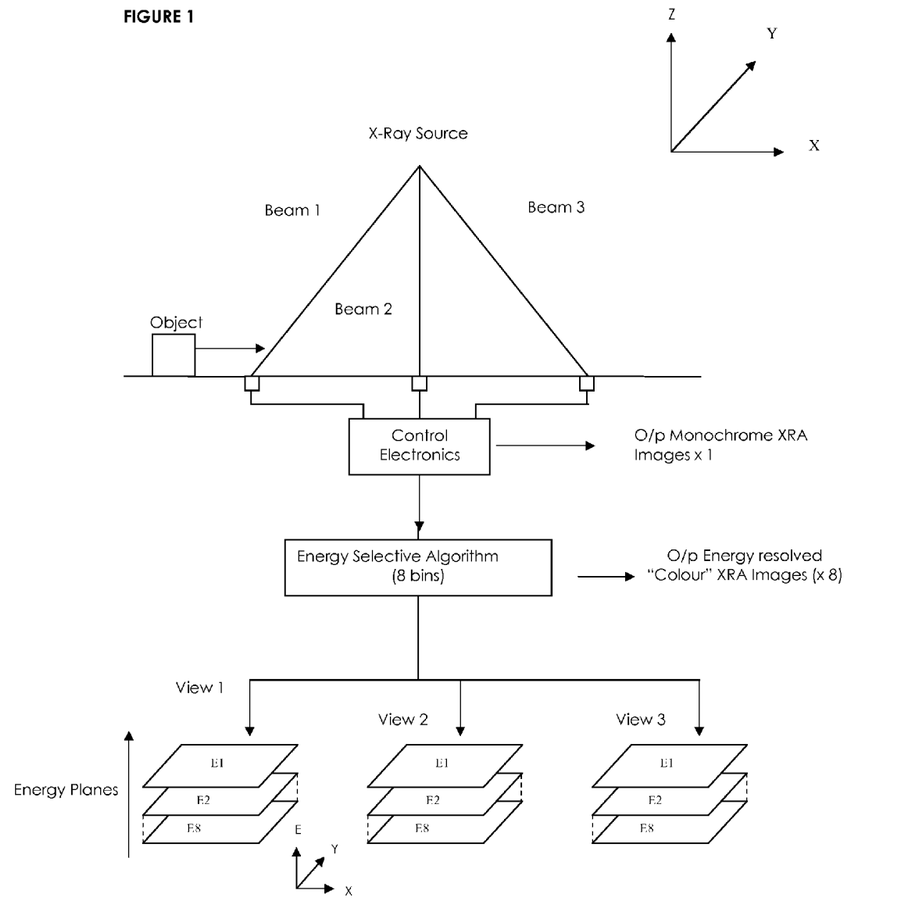
FIG. 1 illustrates a simple schematic of an apparatus in accordance with the invention, including some initial stage data processing modules.

FIG. 1 presents in schematic manner both the apparatus for and the process of collection of transmission data from an object and the initial stages of processing that data in accordance with an embodiment of the invention for illustrative purposes. Apparatus features are presented schematically, and represented in spaced relationship in the figure in such manner that an example order of process steps is presented to some extent in flow chart form. The figure is thus intended to illustrate, in convenient manner, both possible apparatus features and possible process steps of the embodiment of the invention.

In a first stage of the invention, x-ray transmission data is collected from a relatively broad spectrum x-ray source. An object is caused to move through a scanning zone, for example on a suitable continuous conveyance means. Three beam paths from the x-ray source (beam 1, beam 2, beam 3) impinge upon three laterally spaced detectors to obtain transmission information from the object as is passes through each beam, and thus to obtain transmission information from three scanning positions to give three perspective view data sets (here view 1, view 2, view 3).

In the embodiment illustrated, each detector is a linear array of detector elements, and suitable control electronics may be used in association with each detector to build up a two dimensional image in the x, y plane employing the line scan principle which is well established in x-ray radiography. As an object passes through the scanning zone data is collected from the three detector arrays and transmitted to a data collection and processing unit which assembles and collates the data and produces individual perspective view datasets characteristic of the collected data from each detector with spatial resolution in an x, y plane. These are passed to a data storage register.

However, other detector geometries could be envisaged, the overriding requirement being the production of a dataset for each of view 1, view 2 and view 3 which includes intensity information distributed to an appropriate resolution in both the x and y directions.

At this point, the control electronics has resolved a monochromatic representation of intensity information for the source, for example being an average intensity across the whole spectrum of the source, and its potential output is therefore three single monochrome x-ray radiographs, representing an image at each of the three scanning positions. Information can be obtained from such output.

For example, there will be a monocular parallax effect between each pair of such images, which could be exploited in accordance with the principles set out in application number PCT/GB2008/001103 to obtain information presenting at least to some extent a perception of depth. In accordance with that method, images are passed from the data register to be displayed thereon successively and sequentially on suitable display means. The result of this successive sequential display is that an observer viewing the display means is able to glean information from the successive images, and in particular third-dimensional cues, by means of monocular movement parallax between them.

However, in accordance with the invention, each detector is capable of resolving incident information into a plurality of energy bands across at least a substantial part of the source spectrum. In the example, detectors used are capable of spectroscopic resolution of incident x-rays, and in the specific example comprise cadmium telluride although the skilled person will appreciate that other material selections may be appropriate. To exploit this spectral resolution, the x-ray source emits x-ray across a broad energy spectrum. In the example a tungsten source is used, although the skilled person would appreciate that other materials might be appropriate.

Thus, the data which was described above as used to produce monochrome intensity information across the spectrum of the source can be resolved into a plurality of energy bins by use of an energy selection module employing a suitable energy selective algorithm. In the example, eight energy bins are chosen, representing the intensity data at particular energies or energy bands distributed across the spectrum of the source.

Thus, the data at this point comprises 24 datasets of x, y data corresponding respectively to each of the three views in each of the eight energy bins.

It is established that different material compositions can interact with x-ray or similar radiation in an energy selective manner. It is known that the absorption properties of any material can vary with energy, and that the amount by which the absorption properties vary depends in particular on atomic number (in part at least because different absorption effects predominate), density and material thickness.

The transmission of x-rays through a material can be given by the exponential attenuation law, as follows:

$$I/Io = \exp[-(\mu/\rho)\rho t] \quad (1)$$

Where $\mu/\rho$=Mass attenuation coefficient, a material constant which is characteristic of the weighted elemental composition of a material
I=Final intensity
Io=Initial intensity
$\rho$=density of the material
t=thickness of the material Therefore, this energy selected information can give an extra dimension by means of which images of complex objects comprising multiple materials can be de-cluttered and separate elements or components identified more readily. For example, different energy bins may be represented as different colours in a composite image, and an output may be provided of an energy resolved "colour" image having eight "colours" for each of the three views, view 1, view 2 and view 3.

In the alternative, as illustrated at the bottom of FIG. 1, the data can be presented as 24 x, y, intensity datasets, with the differentiated energy as a third pseudo-dimension, and a dataset may be manipulated for imaging based on that structure.

Figure 2:
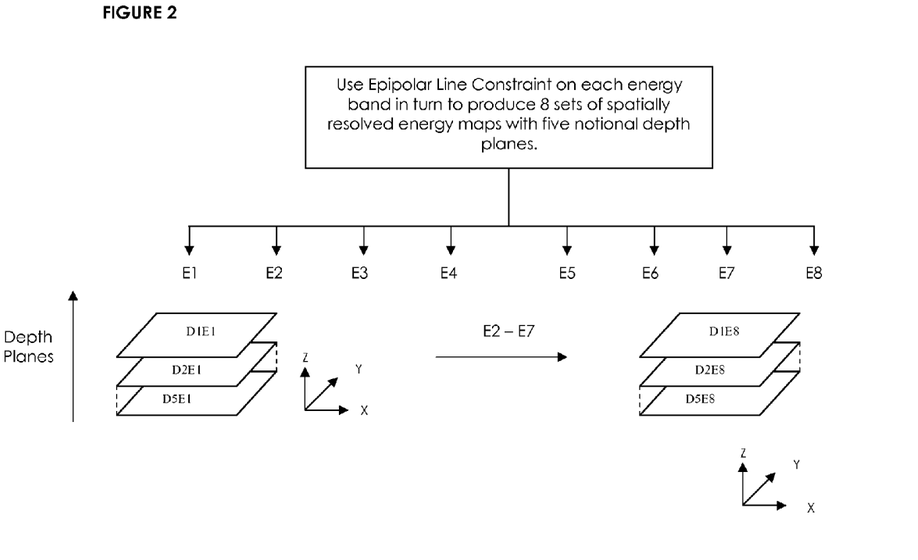
FIGS. 2 and 3 illustrate schematically further process steps/data processing modules to complete the processing of data collected as shown in FIG. 1 in accordance with the principles of the invention.

However, in accordance with the invention, at least a further data processing step is carried out as illustrated in FIG. 2. This is the depth slicing step. As has been indicated above, there will be a disparity between each view of the object owing to parallax effects. This disparity, and in particular the monocular parallax between pairs of images, can be exploited by known numerical image analysis means to identify points of correspondence. In accordance with the embodiment, an image analysis module is made use of which utilises the epipolar line constraint to perform the image analysis in this manner.

The data for each view has already been resolved into eight separate energy bins. Image analysis may be carried out as above for each such bin in turn. It is a particular advantage of the present invention that carrying out the analysis for multiple energy bins may facilitate the identification of points of correspondence using the epipolar line technique.

The image analysis module uses the parallax information to resolve depth data by triangulation, and uses this depth data to divide the original dataset at each view, and for each energy bin, into a plurality of notional depth slices. The number of depth slices chosen is to some extent a matter of choice, and of use of the appropriate numerical analysis algorithm. However the number and density (i.e. depth resolution) is fundamentally limited by the minimum horizontal disparity that can be measured. In this type of system the limiting factor will be the separation between adjacent pixels. The other factor is the angle between the perspective views; the greater this angle then the closer the depth planes will be, although it may be hard to locate conjugate points if the angle is too big. The actual number of depth planes will depend also on the thickness of the object. Using more views can improve the integrity of the finished model by trading off depth plane density vs. accuracy of matching points.

To keep the data manageable for future manipulation, at least three depth slices, and for example 5 to 16, are likely to be preferred.

In the embodiment, appropriate image processing algorithms are used to divide the dataset into five notional depth slices.

As a result of this numerical transformation, the datasets now produced have depth or z-coordinate information represented in the third dimension, in addition to the x, y information inherent in the original data. Effectively, the resultant dataset comprises, for each of the (in the embodiment 8) energy bins, two dimensional (x, y coordinate) transmitted intensity information resolved at each of a desired plurality (in this case 5) of depth planes.

This presents a more powerful and manipulatable dataset than has previously been produced using energy resolved x-ray analysis.

Figure 3:
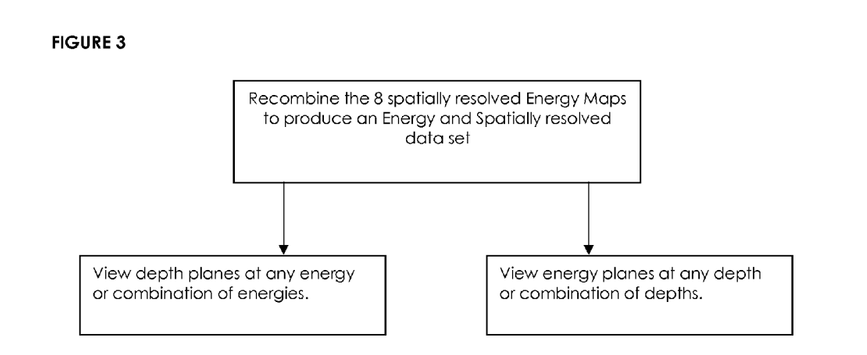

For example, as illustrated in FIG. 3 it is possible to recombine the eight spatially resolved energy maps to produce an energy and spatially resolved dataset, and from this dataset to present imaging information which allows a user to view depth planes at any energy or combination of energies, or to view energy planes at any depth or combination of depths. Either or both of these viewing techniques could be particularly useful to de-clutter images and identify different materials and/or different components of an object under scan made up of complex material or component combinations.

Further, it is known that the transmissive behaviour of materials varies in an energy selective manner with composition, in accordance with the Beer Lambert law (equation (1)

above). This may be used to process the energy selective data numerically to give a more definite materials identification.

For example, in one possible approach, the method is refined by the steps of evaluating a numerical relationship and for example the ratio between intensity data items for at least two pairs of energy bands in a given intensity dataset and for example each successive such energy band to obtain at least one numerical indicator in functional relationship with the mass attenuation coefficient associated with radiation interaction and thus with the intensity dataset; comparing the same with a library of data indicative of such characteristic physical material property for a range of potential component materials, and in particular for example with such physical material property characteristic of target materials such as suspect materials, in order to obtain an indication of the likely material content of material in the scanning zone.

Most of the variables associated with a given scanning event are constant with respect to the frequency/energy of the incident radiation from the source. However, the mass attenuation coefficient varies with energy in a characteristic way. By performing such a ratio analysis on intensity data across at least three different energy bands for a given scanning event to generate at least two ratios, data which is representative of the functional relationship between mass attenuation coefficient and incident radiation energy can be obtained. Thus, inferences relating to the specific mass attenuation coefficient applicable to the transmission path through material under test for a given scanning event can be drawn. A comparison is then made to a suitable database of data representative of the mass attenuation coefficient for different materials and/or target objects to give a more representative indication of what is being scanned.

The technique is particularly powerful for obtaining information for an object comprising multiple component elements or materials, a contained liquid or liquid sample etc, allowing the separate identification of the different components. The technique is particularly powerful when there is some degree of prior knowledge of likely components, and the suitable database of data representative of the mass attenuation coefficient for different materials can be limited to just a few such likely components, and for example likely liquid ingredients.

Figure 4:
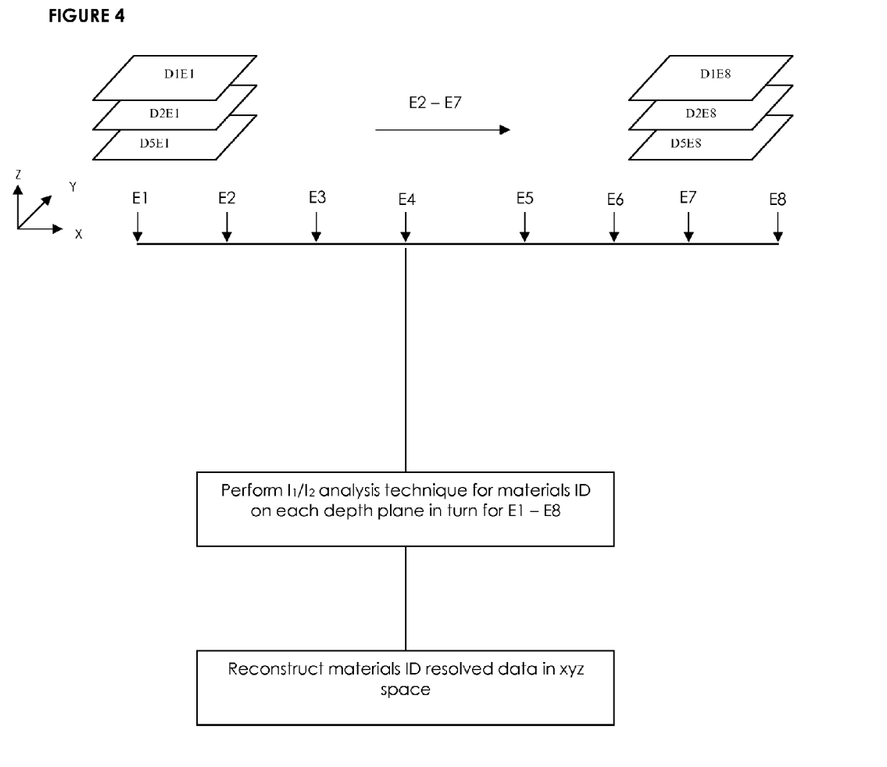
FIG. 4 illustrates possible additional data processing modules/steps to enable further materials identification.
Figure 5:
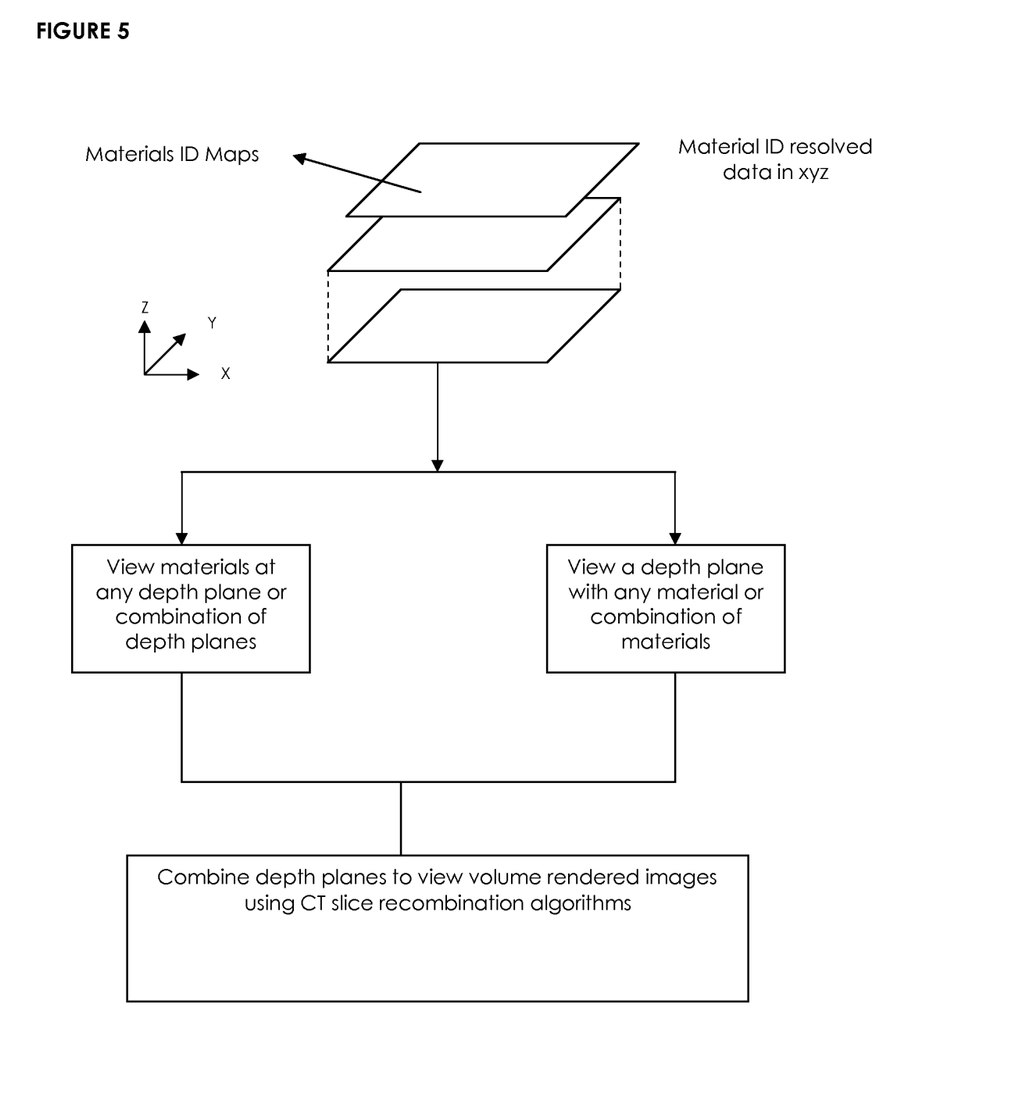
FIG. 5 is example methods of viewing the resolved data in imaging manner.

If this technique is performed on a dataset produced and resolved in accordance with FIGS. 1 and 2 above, then it is possible to reconstruct materials identification resolved data in x, y, z space as illustrated in FIG. 4. The resultant dataset, in this optional embodiment or after this optional additional data step, will allow material identification maps to be produced with full three dimensional resolution as illustrated in FIG. 5. For example it is possible to view selected materials at any depth plane or combination of depth planes, to view a depth plane with any material or combination of materials identified, or to combine depth planes to view volume rendered images using a suitable volume imaging algorithm, such as for example a familiar CT slice recombination algorithm.

Accordingly, the apparatus and method of the invention make it possible to resolve significant amounts of information about the composition of multi-component objects under scan which can be manipulated in a variety of ways to identify materials, and to provide useful means of de-cluttering images of those materials, for example for medical, quality control and security applications.

The invention claimed is:

1. A method for the collection and interpretation of radiographic data from an object comprising the steps of:

providing a radiation source and a radiation detector system spaced therefrom to define a scanning zone there between in such manner as to define at least first and second laterally spaced scanning positions, the detector system being capable of detecting and collecting spectroscopically resolvable information about radiation incident thereon;

causing an object to move relative to and through the scanning zone across the laterally spaced scanning positions; and thereby generating at least a first perspective dataset of intensity information from the detector output at the first scanning position;

generating at least a second perspective dataset of intensity information from the detector output at the second scanning position;

resolving each perspective dataset into at least three spectroscopic energy bands;

for each such resolved spectroscopic energy band:

performing a numerical image analysis of data from each perspective dataset to identify corresponding points in the different perspective datasets;

thereby obtaining numerical data concerning disparity between each perspective dataset;

thereby obtaining z-coordinate information using triangulation and using the z-coordinate information to divide each perspective dataset at each energy band into a plurality of depth slices; and thereby producing a series of output datasets each comprising a 2-D dataset of intensity information resolved to a single energy band and depth slice; wherein a depth resolution step is carried out for each energy band using data from plural perspective views separated at equivalent energy bands to produce an output dataset that includes separate maps of 2-D intensity information for each energy band at each notional depth slice.

2. The method of claim 1 wherein the source radiation is selected from high energy electromagnetic radiation or sub-atomic particle radiation, and the detection system is adapted correspondingly to detect radiation in this spectrum.

3. The method of claim 1 wherein the step of numerically identifying disparity in the collected data from different perspectives makes use of the epipolar line constraint.

4. The method of claim 1 wherein the maps of 2-D intensity information are combined to produce an output dataset having 3-D intensity information for each energy band.

5. The method of claim 1 further comprising the step of generation of an image dataset from at least some of the output datasets having x,y spatial, energy and depth slice resolution.

6. The method of claim 5 further comprising the step of displaying images from such image datasets as separate simultaneously or sequentially displayed images and/or as composite images on a suitable display means.

7. The method of claim 1 in which a perspective dataset is generated by the line scan principle, in that the detector system comprising a plurality of spaced linear detectors capable of generating spectroscopically resolvable information about incident radiation; whereby a perspective dataset is generated by causing an object to move relative to and through the scanning zone whereby to collect data from each of the plurality of spaced linear detectors to generate a corresponding plurality of 2-D perspective datasets in which intensity data is resolved across x,y coordinates.

8. The method of claim 7 wherein the radiation source is collimated to produce a curtain beam.

9. An apparatus for the collection and processing of radiographic data from an object comprising:

a radiation source and a radiation detector system spaced therefrom to define a scanning zone there between configured in such manner as to define at least first and second laterally spaced scanning positions, the detector system being capable of detecting and collecting spectroscopically resolvable information about radiation incident thereon;

a data collection module to collect in use at least a first perspective dataset of intensity information from the detector output at the first scanning position and at least a second perspective dataset of intensity information from the detector output at the second scanning position;

an energy resolution module to process and resolve each perspective dataset into at least three spectroscopic energy bands within the spectrum of the source;

a spatial resolution means including: an image analyzer module to numerically analyse, for each such resolved spectroscopic energy band, data from each perspective dataset to identify corresponding points therein; a disparity module to obtain therefrom numerical data concerning disparity between each perspective dataset; and a depth slicing module to resolve z-coordinate information therefrom using to divide each perspective dataset at each energy band into a plurality of depth slices;

an output data register to store output data generated by the spatial resolution module as a series of output datasets each comprising a 2-D dataset of intensity information resolved to a single energy band and depth slice; wherein the depth slicing module is adapted, for each energy band, to process data from plural perspective views separated at equivalent energy bands to produce an output dataset that includes separate maps of 2-D intensity information for each energy band at each notional depth slice and optionally to combine the maps of 2-D intensity information to produce an output dataset having 3-D intensity information for each energy band.

10. An apparatus in accordance with claim 9 wherein the radiation source comprises a source to deliver high-energy radiation selected from high energy electromagnetic radiation and subatomic particle radiation, and the detection system is adapted correspondingly to detect radiation in this spectrum.

11. An apparatus in accordance with claim 9 wherein the energy resolution module comprises a data processing module to distinguish spectroscopically resolved intensity data and a data storage module to store this intensity data in a suitable plurality of energy bins.

12. An apparatus in accordance with claim 9 further comprising an image generation module to generate an image dataset from at least some and preferably all of the output datasets having x,y spatial, energy and depth slice resolution.

13. An apparatus in accordance with claim 12 further comprising a data register for the storage of said image datasets and/or image display means on which may be displayed images from said image datasets.

14. An apparatus in accordance with claim 9 wherein a detector is adapted to produce spectroscopic resolution in that it is fabricated from a material selected to exhibit inherently as a direct material property a direct variable electrical response to different parts of the source spectrum.

15. An apparatus in accordance with claim 14 wherein the detector comprises a semiconductor material or materials formed as bulk crystal including a Group M-VI semiconductor material.

16. An apparatus in accordance with claim 14 wherein the detector comprises a semiconductor material selected from cadmium telluride, cadmium zinc telluride (CZT), cadmium manganese telluride (CMT) and alloys thereof.

17. An apparatus in accordance with claim 9 operating on the line-scan principle, in that the detector system comprises a plurality of linear detectors capable of generating spectroscopically resolvable information about incident radiation in a laterally spaced serial array at a suitable angular separation such that intensity data may be collected in use from the resultant multiple ray paths between source and array of linear detectors.

18. An apparatus in accordance with claim 17 wherein the radiation source comprises a collimator to produce a curtain beam.

* * * * *

UNITED STATES PATENT AND TRADEMARK OFFICE
CERTIFICATE OF CORRECTION

PATENT NO.         : 8,478,016 B2                                                   Page 1 of 1
APPLICATION NO. : 13/120630
DATED                 : July 2, 2013
INVENTOR(S)       : Max Robinson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 140 days.

Signed and Sealed this
Eighth Day of September, 2015

Michelle K. Lee
*Director of the United States Patent and Trademark Office*